United States Patent
Fabis et al.

(10) Patent No.: US 9,663,779 B2
(45) Date of Patent: *May 30, 2017

(54) NUCLEIC ACID PURIFICATION METHOD

(75) Inventors: Roland Fabis, Leverkusen (DE); Jan Petzel, Solingen (DE); Sabine Scheltinga, Krefeld (DE)

(73) Assignee: QIAGEN GMBH, Hilden (DE)

( * ) Notice: Subject to any disclaimer, the term of this patent is extended or adjusted under 35 U.S.C. 154(b) by 171 days.

This patent is subject to a terminal disclaimer.

(21) Appl. No.: 13/141,885

(22) PCT Filed: Dec. 23, 2009

(86) PCT No.: PCT/EP2009/067878
§ 371 (c)(1),
(2), (4) Date: Sep. 12, 2011

(87) PCT Pub. No.: WO2010/072821
PCT Pub. Date: Jul. 1, 2010

(65) Prior Publication Data
US 2012/0245337 A1 Sep. 27, 2012

(30) Foreign Application Priority Data
Dec. 23, 2008 (DE) ................. 10 2008 063 003

(51) Int. Cl.
C07H 21/00 (2006.01)
C12N 15/10 (2006.01)

(52) U.S. Cl.
CPC .................. *C12N 15/101* (2013.01)

(58) Field of Classification Search
CPC .................................... C12N 15/101
USPC .................. 536/25.4, 25.41, 25.42
See application file for complete search history.

(56) References Cited

U.S. PATENT DOCUMENTS

| 5,599,667 A * | 2/1997 | Arnold et al. ............ 435/5 |
| 2001/0018513 A1* | 8/2001 | Baker .................. 536/25.41 |
| 2005/0239086 A1* | 10/2005 | Lipkin et al. ............ 435/6 |
| 2008/0023395 A1* | 1/2008 | Chen et al. ............ 210/502.1 |
| 2011/0319506 A1* | 12/2011 | Erbacher ............ C12N 15/1006 521/38 |

FOREIGN PATENT DOCUMENTS

| CA | 2 362 979 A1 | 8/2000 |
| JP | 10-502052 A | 10/1995 |
| JP | 9-157282 | 6/1997 |
| JP | 2002-537306 A | 11/2002 |
| JP | 2002-543979 A | 12/2002 |
| JP | 2003-104996 | 4/2003 |
| JP | 2004-501054 A | 1/2004 |
| JP | 2004-521881 A | 7/2004 |
| JP | 2005-520547 A | 7/2005 |
| WO | WO 95/27718 | 10/1995 |
| WO | WO 99/29703 | 6/1999 |
| WO | WO 00/69872 | 11/2000 |
| WO | WO 02/48164 A2 | 6/2002 |
| WO | WO 03/080834 A2 | 1/2003 |
| WO | WO2007/065933 | 6/2007 |
| WO | WO2008/097342 | 8/2008 |

OTHER PUBLICATIONS

Frassineti et al. Nuclear magnetic resonance as a tool for determining protonation constants of natural polyprotic bases in solution. Anal Biochem 1995;231:374-82.*
Porath and Axen. Immobilization of Enzymes to Agar, Agarose, and Sephadex Supports. Methods in Enzymology 1976;44:19-45.*
Blackman. The coordination chemistry of tripodal tetraamine ligands. Polyhedron 2005;24:1-39.*
Anonymous: "QIAGEN Purification Technolgies", Oct. 15, 2005, XP002570999, Retrieved from the Internet: URL:http://wwwl.qiagen.com/reseurces/info/qiagen_Purification_technologies_1.aspx, retrieved on Mar. 2, 2010.
Joachimiak, et al., "Application of spermine-Sepharose column chromatography to the separation of plant-specific transfer ribonucleic acids and aminoacyl-tRNA synthetases" Journal of Chromatography, vol. 180, No. 1, Nov. 28, 1979, pp. 157-162.

* cited by examiner

*Primary Examiner* — Jezia Riley
(74) *Attorney, Agent, or Firm* — Seyfarth Shaw LLP

(57) ABSTRACT

The present invention relates to a method for purifying nucleic acids from a sample containing nucleic acids, the method comprising at least the following steps: a. bringing the sample containing nucleic acids into contact with a nucleic acid binding phase comprising protonatable groups, wherein the protonatable groups have a pKs value of 9 to 12; b. binding the nucleic acids to the nucleic acid phase at a pH (binding pH) that is at least one pH unit less than the pKs value of at least one of the protonatable groups; c. eluting the nucleic acids at a pH greater than the binding pH but at least one pH unit less than the pKs value of at least one of the protonatable groups. Also disclosed are corresponding kits and nucleic acid binding phases that can be used for purifying nucleic acids.

25 Claims, 8 Drawing Sheets

Figure 1:
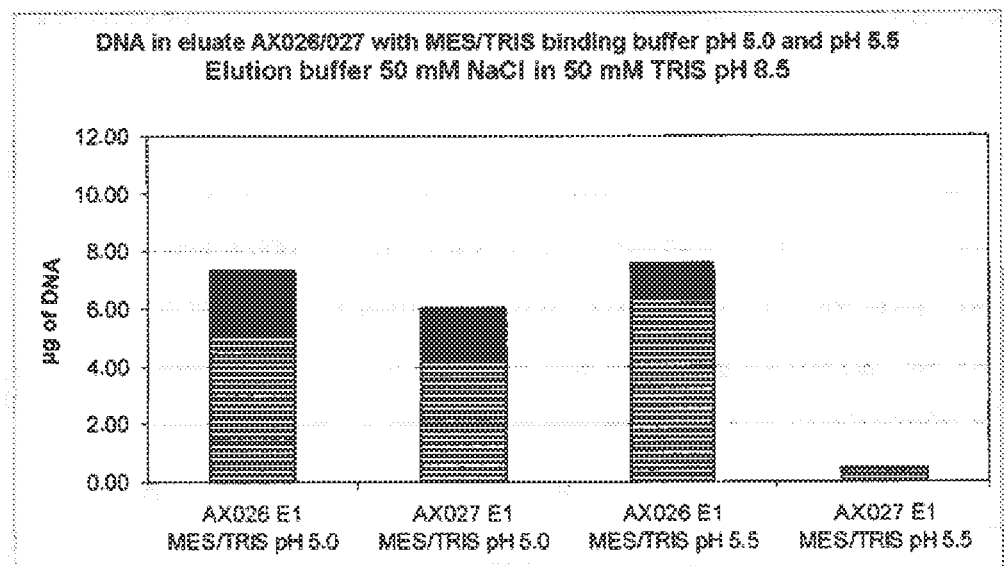

2% strength agarose gel:

Lane 1: crude lysate, lanes 2, 3: breakthroughs, lanes 4, 5: eluates, lane 6: DNA molecular weight marker, 1st band: 500 bases

NUCLEIC ACID PURIFICATION METHOD

This application is a National Stage of PCT/EP2009/067878, filed Dec. 23, 2009 which claims priority to German Application No. 10 2008 063 003.9, filed Dec. 23, 2008, the disclosures of which are incorporated herein by reference in their entirety.

The present invention relates to a method of and a kit for purifying nucleic acids from a nucleic acid-containing sample.

Various methods of purifying and isolating nucleic acids have been disclosed in the prior art. These include the use of phenol chloroform, salting-out methods, the use of ion exchangers and silica particles.

A known method of nucleic acid purification is the "charge-switch method". This involves contacting a nucleic acid-binding phase with a nucleic acid-containing sample at a first pH at which the nucleic acid-binding phase has a positive charge. This favours binding of the negatively charged nucleic acids to said phase. The nucleic acids are released/eluted by adjusting, according to the charge-switch principle, a second pH which is higher than the pKa of the nucleic acid-binding phase, in order to invert, or neutralize, the positive charge. This promotes detachment of the bound nucleic acids from the nucleic acid-binding phase.

The prior art has disclosed both soluble phases (see, for example, EP 0 707 077) and solid phases (see, for example, WO 99/29703). Various solutions are employed for elution, for example solutions having a very high pH or else biological buffers, in particular low-salt buffers such as, for example, Tris buffers, in order to enable the purified nucleic acids to be further processed immediately, for example in an amplification reaction or a restriction digestion.

Even when the known methods of purifying nucleic acids are suitable, there is a need for improving the existing methods, in particular for purifying the nucleic acids in a particularly gentle manner.

It is therefore an object of the present invention to improve the existing methods of purifying nucleic acids.

This object is achieved according to the present invention by a method of purifying nucleic acids from a nucleic acid-containing sample, which has at least the following steps:

a. contacting the nucleic acid-containing sample with a nucleic acid-binding phase having nucleic acid-binding groups, said nucleic acid-binding groups having at least one protonatable group having a pKa of from 9 to 12;

b. binding the nucleic acids to the nucleic acid-binding phase at a pH (binding pH) which is at least one pH unit below the pKa of at least one of the protonatable groups;

c. eluting the nucleic acids at a pH which is above the binding pH but at least one pH unit below the pKa of at least one of the protonatable groups (elution pH).

The present invention relates to the purification of nucleic acids by means of a nucleic acid-binding phase which correspondingly has nucleic acid-binding groups. Such a nucleic acid-binding group has at least one protonatable group whose pKa is from 9 to 12. The nucleic acids are bound at a pH below the pKa of at least one of these protonatable groups. The protonatable groups take up a proton and, as a result, become positively charged, causing the nucleic acid-binding phase to bind the negatively charged nucleic acids. The elution is carried out at a higher pH, thereby reducing the positive charge of the nucleic acid-binding phase. According to the invention, however, the elution pH is below the pKa of the protonatable groups, in particular at least one pH unit below, preferably at least two pH units below. This has the considerable advantage of enabling the elution to be carried out also under gentle conditions. In contrast to the prior art, the present invention therefore allows elution at a pH which is below the pKa of the protonatable groups.

According to one embodiment of the present invention, the nucleic acids are bound at a pH of from 3 to 8. This information relates to the pH during binding and therefore in the sample. Depending on the design of the solid phase, the method according to the invention can also be carried out at very gentle conditions, thus enabling the nucleic acids to be bound even at a pH of from 4 to 7.5, preferably from 5 to 7.5, particularly preferably from 5 to 7, and very particularly preferably from 6.5 to 7, and therefore in the virtually neutral range. Owing to the fact that the protonatable groups of the nucleic acid-binding phase have a pKa of from 9 to 12, said groups have even at relatively neutral pH values a positive charge which is sufficient for allowing effective attachment of the nucleic acids. Binding can therefore be carried out under very gentle conditions, preventing the nucleic acids from damage.

In addition, it has proved to be advantageous to perform binding at a low salt concentration. According to one embodiment, the salt concentration is therefore less than 1 M during binding of the nucleic acids to the nucleic acid-binding phase. Preferably, the salt concentration is less than 0.5 M, less than 0.25 M or even less than 0.1 M. A low salt concentration is preferred in order to optimize binding of the nucleic acids to the solid phase. Ion concentrations which are too high have an adverse influence on the ionic interactions of nucleic acid and the nucleic acid-binding phase. We have found that the binding buffer may also contain certain amounts of organic substances such as, for example, carbohydrates, alcohols such as ethanol, methanol, for example, or acetone and acetonitride. These substances do not impair binding.

Another important step of the present method is elution of the nucleic acids. As illustrated, the nucleic acids are released at a pH which is above the binding pH. Consequently, the protonatable groups have a smaller positive charge during elution, and this favours the release of the nucleic acids. In addition, the pH during elution is at least one pH unit below the pKa of at least one of the protonatable groups of the nucleic acid-binding phase. As a result of this, as illustrated above, the elution can be carried out under particularly gentle conditions.

Depending on the nucleic acid-binding group or nucleic acid-binding phase employed, the elution is preferably carried out at a pH of from 7.5 to 11, from 7.5 to 10, preferably at a pH of from 8 to 9 or 8.2 to 8.8. These low pH values achieve particularly advantageous results because the nucleic acids are released in a particularly gentle way. Further measures which enable the nucleic acids to be released at a low pH in a particularly efficient manner are described below.

In order to enable the isolated nucleic acids to be further processed immediately in the elution buffer, the latter preferably has a low salt concentration. According to one embodiment, the salt concentration is therefore less than 1 M, preferably less than 0.5 M, less than 0.25 M, less than 0.1 M, particularly preferably less than 50 mM, less than 25 mM or even less than 10 mM. Suitable salts may be chlorides of alkali metals and alkaline earth metals or ammonium, other salts of mineral acids, acetates, borates, and compounds such as Tris, Bis-Tris, and organic buffers such as, for example, MES, CHAPS, HEPES, and the like. In addition, substances suitable for elution have been disclosed in the prior art.

To facilitate purification, preferably at least one washing step is carried out after binding and prior to elution of the nucleic acids. Preference is given to using aqueous solutions with low salt concentrations but also water for washing. Preference is given to salts present in the washing buffers being at a concentration of less than 400 mM, particularly preferably less than 200 mM, 100 mM, 50 mM and/or even less than 25 mM. The washing buffer may contain organic components, for example alcohols, polyols, polyethylene glycols, acetone, acetonitride or carbohydrates. However, the washing buffers may be without interfering amounts of the corresponding organic components, so as not to impair subsequent applications such as, for example, enzymic processing, amplification reactions and the like ("downstream" applications).

The nucleic acid-binding phase to be employed according to the invention may be solid or soluble. Soluble nucleic acid-binding phases usually precipitate nucleic acids at the binding pH and release the bound nucleic acids from the precipitate again at the elution pH. Soluble nucleic acid-binding phases or polymers are described in the prior art, for example in EP 0 707 077.

According to the preferred embodiment, the nucleic acid-binding phase is a solid phase. For preparation, the protonatable groups may be bound, for example, to a solid support material. Details will be described hereinbelow. Using a solid phase facilitates removal of the bound nucleic acids from the sample. According to one embodiment, binding of the nucleic acids is therefore followed by removal of the solid phase.

According to one embodiment, the protonatable groups are or have ion exchangers, preferably anion exchangers. Preferred protonatable groups proven for binding of nucleic acids are amino groups, with preference being given to primary and secondary amino groups. The amino groups preferably have a pKa of from 9 to 12, preferably 10 to 12. The nucleic acid-binding group preferably has from 1 to 10, particularly preferably 2 to 8 and in particular 2 to 6, amino groups. Examples of preferred nucleic acid-binding groups are primary, secondary and tertiary mono- and polyamines. These may be substituted or unsubstituted. Examples are in particular amines of the formulae $R_1R_2R_3N$, $R_1R_2N(CH_2)_nNR_3R_4$ $R_1R_2N(CH_2)_nNR_3(CH_2)_mNR_4R_5$ $R_1R_2N(CH_2)_nNR_3(CH_2)_mNR_4(CH_2)_oNR_5R_6$ $R_1R_2N(CH_2)_nNR_3(CH_2)_mNR_4(CH_2)_oNR_5(CH_2)_pNR_6R_7$ $R_1R_2N(CH_2)_nNR_3(CH_2)_mNR_4(CH_2)_oNR_5(CH_2)_pNR_6(CH_2)_qNR_7R_8$ $R_1R_2N(CH_2)_nNR_3(CH_2)_mNR_4(CH_2)_oNR_5(CH_2)_pNR_6(CH_2)_qNR_7(CH_2)_rNR_8R_9$ $R_1R_2N(CH_2)_nNR_3(CH_2)_mNR_4(CH_2)_oNR_5(CH_2)_pNR_6(CH_2)_qNR_7(CH_2)_rNR_8(CH_2)_sNR_9R_{10}$ where
n, m, o, p, q, r and s are, independently of one another, 2 to 8;

$R_1$, $R_2$, $R_3$, $R_4$, $R_5$, $R_6$, $R_7$, $R_8$, $R_9$ and $R_{10}$ are identical or different and are selected from the group consisting of H, alkyl (branched or unbranched) and aryl.

Preferred nucleic acid-binding groups are particularly N-propyl-1,3-propanediamine and pentaethylenehexamine and very particularly spermine and spermidine.

In addition, it is also possible to use cyclic amines, aromatic amines or amino-functionalized heterocycles. The amines may bear substituents, for example alkyl, alkenyl, alkynyl or aromatic substituents, and additionally the hydrocarbon chains may also be closed into a ring. The hydrocarbon chains may also have heteroatoms, such as oxygen, nitrogen, sulphur or silicon, or branchings.

Other suitable nucleic acid-binding groups are polyoxyalkyleneamines having one, two of three amino groups. These are available, for example, under the name "Jeffamine" polyoxyalkyleneamines. Jeffamines contain primary amino groups which are bound to the terminals of the polyether backbone. The polyether backbone may be based on propylene oxide, ethylene oxide or mixtures thereof; the use of other backbone segments is also conceivable.

As stated, the amino groups of the amines have pKa values of from 9 to 12, preferably from 10 to 12.

According to the invention, it is also possible to use mixtures of the corresponding nucleic acid-binding groups or to apply them on a support.

The nucleic acid-binding groups such as, for example, the amines may be bound to the support covalently or by electrostatic, polar or hydrophobic interaction. Preference is given to linking them in such a way that one (e.g. N-propyl-1,3-propanediamine) to ten, preferably two to eight, particularly preferably two to six, amino groups are present by way of a protonatable group per attached group.

Preferably, the amino groups of the nucleic acid-binding groups are not conjugated to an electron density-reducing group such as, for example, a carboxyl group, a carbonyl group, a group with C—C double bonds or a β-hydroxyethyl group and, as a result, their pKa is between 9 and 12. Conjugation to an electron density-reducing group is regarded to be present, if an amino function and the corresponding, electron density-reducing group are connected via only three, two or less carbon atoms.

According to a preferred embodiment, the nucleic acid-binding groups are bound to a support for a solid nucleic acid-binding phase to be used for nucleic acid purification. Examples of suitable supports for the nucleic acid-binding groups are organic polymers such as polystyrene and its derivatives, polyacrylates and polymethacrylates, and their derivatives, or polyurethanes, nylon, polyethylene, polypropylene, polybutylene, and copolymers of thebe materials. In addition, these nucleic acid-binding groups may also be linked to polysaccharides, in particular hydrogels such as agarose, cellulose, dextran, cross-linked dextran gel sold under the trademark SEPHADEX®, allyl dextran and N,N'-methylenebisacrylamide matrix sold under the trademark SEPHACRYL®, or chitosan, Furthermore, the nucleic acid-binding groups may also be attached to inorganic supports such as, for example, silica gel, glass or other metal oxides and semi-metal oxides, silica, boron oxide or metal surfaces such as, for example, gold. Magnetic particles are particularly advantageous with regard to handling. The nucleic acid-binding groups may be bound to said supports directly or else via "spacers". They may also be part of a larger molecule, Examples of spacers are hydrocarbon chains, polyethylene glycols or polypropylene glycols, and functionalized silanes, Said spacers may be branched or unbranched.

Chemical functionalities which may be employed for attaching the nucleic acid-binding groups are acid amides or acid anhydrides, epoxides, tresyl groups, formyl groups, sulphonyl chlorides, maleimides or carbodiimide chemistry-activated carboxylate groups. It is likewise possible within the scope of the invention to attach the nucleic acid-binding groups such as, for example, amines non-covalently, for example by ionic interactions or by absorptive processes. The nucleic acid-binding groups may also be attached via thiols to gold surfaces, for example. Preference is given to attaching the nucleic acid-binding groups to carboxylated surfaces.

Other embodiments of the support materials comprise non-magnetic and magnetic particles, column materials, membranes, and surface coatings. Mention may also be made of functionalized supports such as tubes, membranes, non-wovens, paper, reaction vessels such as PCR vessels, "Eppendorf tubes", multiplates, chips and microarrays.

Another embodiment of the present invention relates, as stated, to a soluble polymer which has protonatable groups in accordance with the present invention and which is capable of reversibly binding nucleic acids according to the principle according to the invention. Examples of suitable soluble phases which may also be modified according to the invention are described, for example, in EP 0 707 077. The preferred solvent is water but it is also possible to employ polymers which have been functionalized according to the invention and which are soluble in organic solvents such as ethanol, for example.

Surprisingly, we have found that the applicable pH values and salt concentrations in the binding and elution buffers correlate with the number of protonatable groups, in particular amino groups, present per nucleic acid-binding group. Thus, at a salt concentration of approx. 50 mM, the nucleic acid binds to spermine-coated surfaces even at pH 6, while a lower pH of 5.5, preferably even 5, is preferred for application of an N-propyl-1,3-propanediamine-coated surface. Elution from N-propyl-1,3-propanediamine surfaces is successful even at pH 7.5, while a pH of approx. 8.5 is required with spermine-coated surfaces at a salt concentration of 50 mM. However, the pH may also still be lowered for elution by modifying the support (see below).

An efficient elution and consequently detachment of the bound nucleic acids from the nucleic acid-binding phase is particularly important for the efficiency of nucleic acid purification. Here, it was surprisingly found that it is not only the pKa values of the protonatable groups of the nucleic acid-binding groups that are important. The structure of the nucleic acid-binding phase and the presence of other functional groups also contribute to facilitating and improving elution at pH values in the neutral or weakly alkaline range.

According to one embodiment, the nucleic acid-binding phase additionally bears functional groups which promote elution of the nucleic acids at the elution pH, for example by exerting a repelling effect. These functional groups therefore preferably have a negative charge during elution. The pKa values of these groups may be, for example, in a range from 0 to 7, preferably 1 to 5. Suitable are, for example, ion exchangers, in particular cation exchangers, preferably acidic groups such as, for example, carboxyl groups. Other suitable groups are betaines, sulphonates, phosphonates and phosphates. For example, the solid support may be functionalized with carboxyl groups to enable the nucleic acid-binding groups to be attached. The concentration of the nucleic acid-binding groups for attachment will be chosen in such a way that some of the carboxyl groups are free and therefore not functionalized with the nucleic acid-binding groups. These groups do not impair binding of the nucleic acids at low pH values. At higher pH values, however, they are preferably negatively charged and, as a result, facilitate detachment of the nucleic acids from the nucleic acid-binding groups. This interaction may also be facilitated by selection of the length or the distance between the protonatable groups of the nucleic acid-binding groups and the negative-ionizable groups such as, for example, the carboxyl groups. This advantageously facilitates elution at low pH values, thus increasing the yield. The selection, strength and length of the functional groups exerting a repelling effect on the nucleic acids at the elution pH vary, depending on the nucleic acid-binding group selected, thus in particular the number of protonatable groups per nucleic acid-binding group and their distance to the elution-promoting functional groups.

We have furthermore demonstrated that the elution efficiency can also be increased if the nucleic acid-binding/protonatable groups are arranged at a distance to one another on the support material or diluted. According to one embodiment, such an arrangement of the nucleic acid-binding groups can be achieved by coating the support only with small amounts of nucleic acid-binding groups. Preference is therefore given to carrying out functionalization with a substoichiometric amount of nucleic acid-binding groups. As a result, the nucleic acid-binding groups are basically diluted on the support and, consequently, fewer nucleic acid-binding groups are available. This facilitates elution because the nucleic acids bind less tightly and can therefore be detached again more readily from the nucleic acid-binding phase. For example, only ≤50%, ≤25%, ≤15%, ≤10% or only ≤5% of the functional groups on the support material may be functionalized with nucleic acid-binding groups. If the support material does not have any suitable functional groups for attaching the nucleic acid-binding groups, the support material may be functionalized first in order to provide it with suitable functional groups (see above). To this end, the appropriate profile of coating of the support material with a substoichiometric amount of nucleic acid-binding groups may also be achieved by providing the support material correspondingly with fewer functional groups for attaching said nucleic acid-binding groups.

According to another embodiment, the support is coated with a mixture of nucleic acid-binding groups and "diluting groups". The term "diluting groups" is used herein for illustrating its function in relation to the nucleic acid-binding groups. Their function comprises adjusting the amount of nucleic acid-binding groups on the support and thereby also influencing the strength of binding of the nucleic acids. The higher the proportion of diluting groups, the fewer nucleic acid-binding groups are applied to the support and the lower is the strength of binding to the nucleic acids. The diluting groups may have a negative, positive or neutral charge or ionizable groups. Consequently, the diluting groups may simultaneously also have functional groups which promote elution (see above). The proportion of nucleic acid-binding groups in relation to the diluting groups may be, for example, ≤50%, ≤25%, ≤15%, ≤10% or only ≤5%. Examples of suitable diluting groups are amines, dimethylamine, diethylamine and ammonia. According to a preferred embodiment, a mixture of common (known in the prior art) monoamines and polyamines according to the invention is applied to the support. The polyamines in this combination are used for attaching the nucleic acids, with the monoamines acting primarily as diluting groups. An example of a suitable diluting group would be ethanolamine.

The pH of the nucleic acid-binding phase may be optimized with respect to the elution conditions by choosing/combining the parameters described, in particular the functional groups promoting elution, the diluting groups, and the dilution or mixture with nucleic acid-binding groups. Correspondingly, the elution profile of the nucleic acid-binding phase, in particular the elution pH, may be controlled or adjusted.

Nucleic acids which may be purified by the systems according to the invention may he present in body fluids such as blood, urine, stool, saliva, sputum, or other body fluids, in biological sources such as tissue, cells, in particular animal cells, human cells, plant cells, bacterial cells and the like, organs such as liver, kidneys or lungs, etc. In addition, the nucleic acid may he obtained from support materials such as swabs, pap smears, and stabilizing media such as the methanol-water solution sold under the trademark PRESERVCYT® or the liquid-based Pap test sold under the trademark SUREPATH®, or else from other liquids such as, for example, juices, aqueous samples or food in general. In addition, the nucleic acids may be obtained from plant material, bacterial lysates, paraffin-embedded tissue, aqueous solutions or gels.

In addition, the present invention relates to the use of a nucleic acid-binding phase as described above for purifying nucleic acids. The nucleic acid-binding phase employed according to the invention has in particular nucleic acid-binding groups with at least one protonatable group having a pKa of from 9 to 12. Preferred embodiments are described in detail above (see disclosure above) and are characterized in particular by one or more of the following features:
  a) the nucleic acid-binding phase is solid or soluble; and/or
  b) the nucleic acid-binding phase has nucleic acid-binding groups bound to a solid support; and/or
  c) the nucleic acid-binding phase additionally has functional groups which promote release/elution of the nucleic acids at the elution pH, preferably cation exchangers, in particular carboxyl groups; and/or d) the nucleic acid-binding phase according to feature b) or c) has a support selected from the group consisting of organic polymers such as polystyrene and its derivatives, polyacrylates and polymethacrylates and their derivatives, polyurethanes, nylon, polyethylene, polypropylene, polybutylene and copolymers of these materials, polysaccharides and hydrogels such as agarose, cellulose, dextran, cross-linked dextran gel sold under the trademark SEPHADEX®, allyl dextran and N,N'-methylenebisacrylamide matrix sold under the trademark SEPHACRYL®, chitosan, inorganic supports, in particular silica gels, silica particles, glass or other metal and semi-metal oxides, boron oxide, supports with metal surfaces, for example gold and magnetic particles; and/or
  e) the nucleic acid-binding groups of the nucleic acid-binding phase are amines, in particular primary and secondary amines; and/or
  f) the nucleic acid-binding groups according to feature e) are in particular spermine and/or spermidine.

The invention further provides a kit for purifying nucleic acids, which kit is characterized in that it has
  a) a nucleic acid-binding phase according to the invention, which has nucleic acid-binding groups with at least one protonatable group having a pKa of from 9 to 12;
  b) a binding buffer with a pH which is at least one pH unit below the pKa of at least one of the protonatable groups of the nucleic acid-binding phase, and/or a binding buffer which enables such a pH to be adjusted in the sample;
  c) an elution buffer with a pH which is at least one pH unit below the pKa of at least one of the protonatable groups of the nucleic acid-binding phase but above the pH of the binding buffer, and/or an elution buffer which enables such a pH to be adjusted in the sample.

Details of the nucleic acid-binding phase and the elution conditions are described above and also apply in connection with the kit according to the invention and characterize the components/buffers used therein. Reference is made to the disclosure above. In addition, the kit may contain other customary components such as, for example, lyses, washing and/or neutralizing reagents and/or buffers.

The binding buffer may preferably have at least one of the following features:
  i. a pH of from 3 to 8; and/or
  ii. a pH of from 4 to 7.5; and/or
  iii. a pH of from 4.5 to 7; and/or
  iv. a pH of from 5.5 to 7; and/or
  v. a pH of from 6.5 to 7; and/or
  vi. a salt concentration of less than 1 M, less than 0.5 M, less than 0.25 M or less than 0.1 M.

The advantages of the corresponding features have been illustrated above in connection with the method, and reference is made to the disclosure above.

The elution buffer according to the invention may have at least one of the following features:
  i. a pH of from 7.5 to 10; and/or
  ii. a pH of from 8 to 9; and/or
  iii. a pH of from 8.2 to 8.8; and/or
  iv. a salt concentration of less than 1 M, less than 0.5 M, less than 0.25 M, less than 0.1 M, less than 25 mM, less than 15 mM, or less than 10 mM; and/or
  v. it is selected from the group consisting of water, biological buffers, organic buffers, in particular Tris, Tris-Bis, MES, CHAPS and HEPES.

Details and advantages of the corresponding features have been illustrated above in connection with the method according to the invention. Reference is made to the disclosure above.

The corresponding kits may be applied in particular within the framework of the method according to the invention. The present methods, kits and nucleic acid-binding solid phases may be employed in particular in the field of molecular biology, molecular diagnostics, in forensics, in food analysis and in applied testing.

Preference is given to enabling the eluted nucleic acids to be further processed immediately, thus to be used, for example, in a PCR, RT-PCR, a restriction digestion or a transcription. Further purification is not required, as long as the elution buffers are designed as described above and preferably have a low salt concentration.

Nucleic acids suitable for purification are DNA and RNA, in particular genomic DNA, plasmid DNA, and also PCR fragments, cDNA, miRNA, siRNA, and also oligonucleotides and modified nucleic acids such as, for example, PMA or LMA. It is also possible to purify viral or bacterial RNA and DNA or nucleic acids from human, animal or plant sources. Furthermore suitable for a purification according to the invention are also DNA/RNA hybrids.

The present invention will be illustrated below on the basis of some examples. These examples are not limiting but are preferred embodiments of the present invention. In addition, all references cited herein are made subject matter of the disclosure.

EXAMPLES

Model systems of nucleic acids that were employed in the experiments are pUC21 plasmid DNA, uncut, RNA, and genomic DNA. In addition, the purification of nucleic acid fragments of different sizes was demonstrated using plasmid DNA cut into fragments by restriction enzymes.

The procedure (in the experimental part) followed the preparation protocols A) to I) below:

A) Reaction of Magnetic Polymers with Amines

Materials

Magnetic polymer: Carboxylate-modified magnetic particles sold under the trademark SERA-MAG® Double Speed Magnetic Carboxylate-Modified Microparticles (dsMGCM) catalogue No. 65152105050250, 5% strength aqueous suspension, or Magnetic Carboxylate-Modified (MG-CM), catalogue No. 2415-2105, 5% strength aqueous suspension, Seradyn Inc. Indianapolis, USA.

Amines: spermine (Fluka, 85590), spermidine (Fluka, 85561), propyl-1,3-propanediamine (Aldrich, catalogue No. 308153), pentaethylenehexamine (Aldrich, catalogue No. 292753) poly(allylamine hydrochloride), Mw 15 000 (Aldrich, catalogue No. 283215)

500 mg of the magnetic particles are resuspended in 10 ml of 50 mM MES buffer, pH 6.1, and then admixed with 11.5 ml of a 50 mg/ml solution of N-hydroxysuccinimide. After mixing using a minishaker, 10 ml of a 52 μmol/l solution of 1-ethyl-3-(3-dimethylaminopropyl) carbodiimide (EDC) are added; followed by another vortexing. The solution is then left to react on an end-over-end shaker for 30 minutes, and the supernatants are then removed. After resuspension in 50 ml of 50 mM MES buffer, pH 6.1, the suspension is distributed in 10 ml aliquots. The suspension is magnetically separated and the supernatants are discarded. After suspension in 1 ml of 50 mM MES buffer, pH 6.1, in each case 2 ml of the amine are added at a concentration of 100 mg/ml in 50 mM MES and a pH 8.5, followed by thorough vortexing, sonication for 10 minutes, and the suspension is left to react on an end-over-end shaker for one hour. This is followed by washing twice with in each case 10 ml of 50 mM MES buffer, pH 6.1, magnetic separation and discarding of the supernatants. The particles are then resuspended in each case 2 ml of MES buffer at pH values from 4.5 to 7.0.

B) Purification of Plasmid pUC21 Using N-propyl-1,3-propanediamine-functionalized Magnetic Polymers (AX027)

2 mg of the magnetic particles in 50 mM MES buffer, pH 5.0 or 5.5 are used and admixed in each case with 50 μl of 50 mM MES buffer, pH 5.0 or 5.5. This is followed by adding 10 μg of plasmid pUC21 in 10 μl of buffer "EB" (QIAGEN, catalogue No. 19068) and mixing by way of brief shaking. The reaction mixture is then incubated on an end-over-end shaker or Eppendorf shaker for 5 minutes. The sample mixture is magnetically separated and the supernatants are removed and the DNA content is determined photometrically. The residues are then washed twice with in each case 100 μl of Millipore water, magnetically separated, and the supernatants are discarded. This is followed by eluting twice by adding in each case 50 μl of 50 mM Tris buffer, pH 8.5 with NaCl concentrations of 50 mM, 100 mM, 200 mM and 400 mM, removal by means of magnetic separation and examining the eluates photometrically for their DNA content.

FIG. 1 depicts the results for 50 mM NaCl concentrations, also in comparison with AX 026 and AX 027.

C) Purification of Plasmid pUC21 Using Spermidine-functionalized Magnetic Polymers (AX 026)

2 mg of the magnetic particles in 50 mM MES buffer, pH 6.2 are used and admixed with 50 μl of 50 mM Tris buffer, pH 6.2. This is followed by adding 10 μg of plasmid pUC21 in 10 μl of buffer "ES" (QIAGEN, catalogue No. 19068) and mixing by way of brief shaking. The reaction mixture is then incubated on an end-over-end shaker or Eppendorf shaker for 5 minutes. The sample mixture is magnetically separated and the supernatants are removed and the DNA content is determined photometrically. The residues are then washed twice with in each case 100 μl of Millipore water, magnetically separated, and the supernatants are discarded. This is followed by eluting twice by adding in each case 50 μl of 50 mM Tris buffer, pH 7.5, 8.0 and 8.5 with NaCl concentrations in each case of 50 mM, 100 mM, 200 mM and 400 mM, removal by means of magnetic separation and examining the eluates photometrically for their DNA content.

Figure 2:
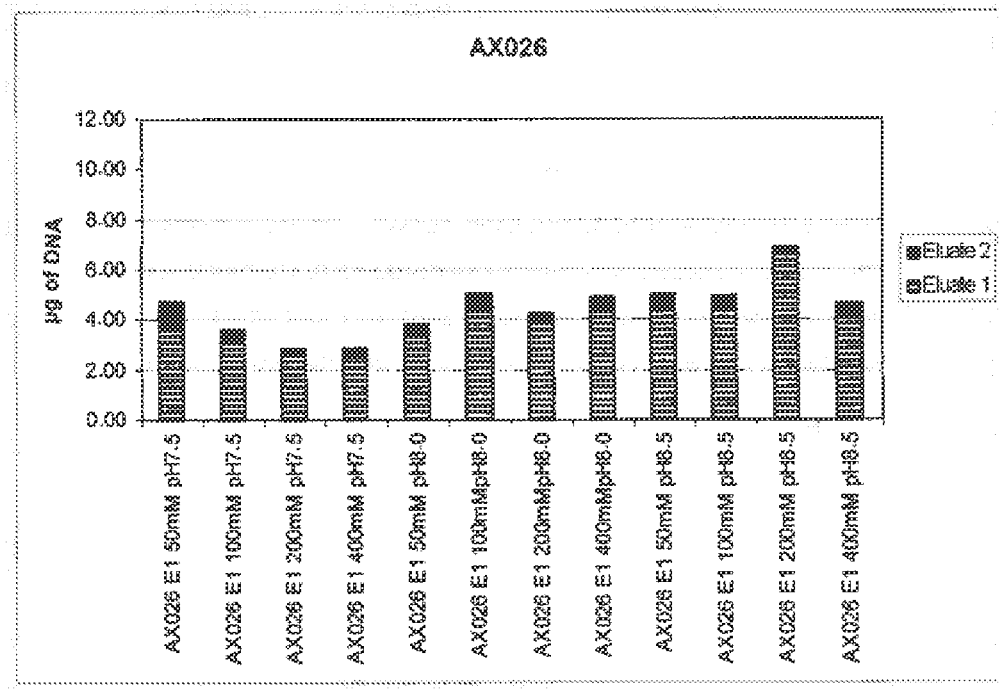

The results are depicted in FIG. 2.

D) Purification of Plasmid pUC21 Using Spermine-functionalized Magnetic Polymers (AX 025)

2 mg of the magnetic particles in 50 mM MES buffer, pH 6.1 are used and admixed with 50 μl of 50 mM Tris buffer, pH 7.0. This is followed by adding 10 μl of plasmid pUC21 in 10 μl of buffer "EB" (QIAGEN, catalogue No. 19068) and mixing by way of brief shaking. The reaction mixture is then incubated on an end-over-end shaker or Eppendorf shaker for 5 minutes. The sample mixture is magnetically separated and the supernatants are removed and the DNA content is determined photometrically. The residues are then washed twice with in each case 100 μl of Millipore water, magnetically separated, and the supernatants are discarded. This is followed by eluting twice by adding in each case 50 μl of 50 mM Tris buffer, pH 7.5, 8.0 and 8.5 with NaCl concentrations in each case of 50 mM, 100 mM, 200 mM and 400 mM, removal by means of magnetic separation and examining the eluates photometrically for their DNA content.

Figure 3:
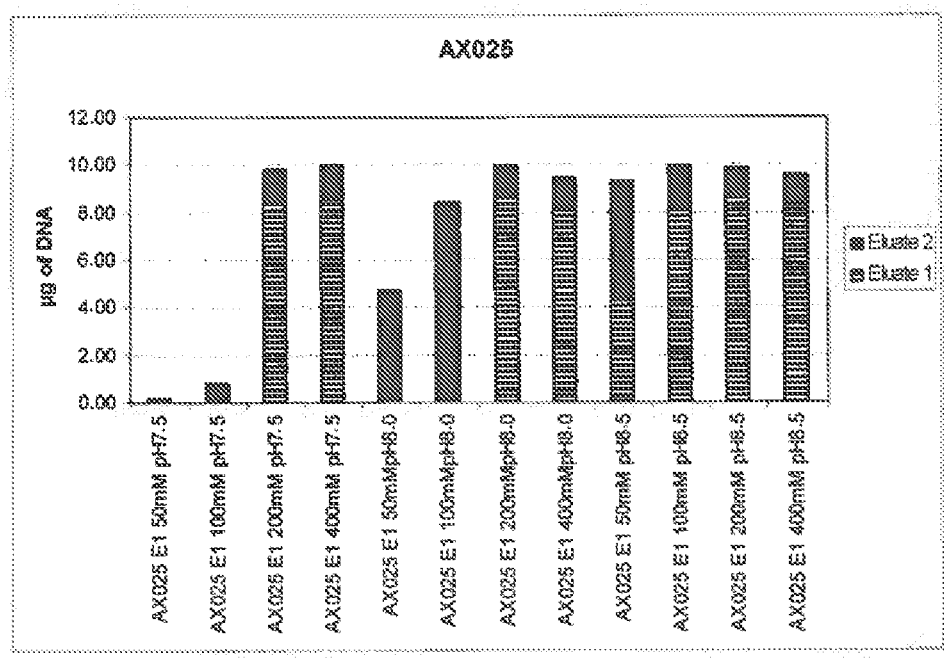

The results are depicted in FIG. 3.

E) Purification of Plasmid pUC21 Using Pentaethylenehexamine-functionalized Magnetic Polymers (AX 028)

2 mg of the magnetic particles in 50 mM MES buffer, pH 6.1 are used and admixed with 50 μl of 50 mM Tris buffer, pH 7.0. This is followed by adding 10 μg of plasmid pUC21 in 10 μl of buffer "EB" (QIAGEN, catalogue No. 19068) and mixing by way of brief shaking. The reaction mixture is then incubated on an end-over-end shaker or Eppendorf shaker for 5 minutes. The sample mixture is magnetically separated and the supernatants are removed and the DNA content is determined photometrically. The residues are then washed twice with in each case 100 μl of Millipore water, magnetically separated, and the supernatants are discarded. This is followed by eluting twice by adding in each case 50 μl of 50 mM Tris buffer, pH 7.5, 8.0 and 8.5 with NaCl concentrations in each case of 50 mM, 100 mM, 200 mM and 400 mM, removal by means of magnetic separation and examining the eluates photometrically for their DNA content.

Figure 4:
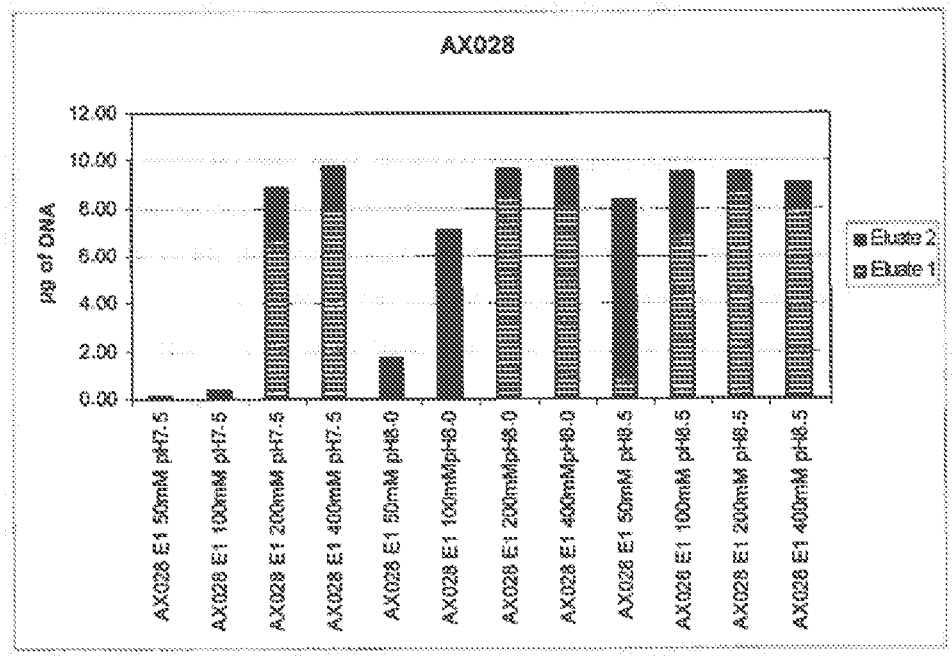

The results are depicted in FIG. 4.

F) Purification of Plasmid pUC21 Using Polyallylamine-functionalized Magnetic Polymers (AX 029)—Comparative Example 2 mg of the magnetic particles in 50 mM MES buffer, pH 6.1 are used and admixed with 50 μl of 50 mM Tris buffer, pH 7.0. This is followed by adding 10 μg of plasmid pUC21 in 10 μl of buffer "EB" (QIAGEN, catalogue No. 19068) and mixing by way of brief shaking. The reaction mixture is then incubated on an end-over-end shaker or Eppendorf shaker for 5 minutes. The sample mixture is magnetically separated and the supernatants are removed and the DNA content is determined photometrically. The residues are then washed twice with in each case 100 µl of Millipore water, magnetically separated, and the supernatants are discarded. This is followed by eluting twice by adding in each case 50 µl of 50 mM Tris buffer, pH 7.5, 8.0 and 8.5 with NaCl concentrations in each case of 50 mM, 100 mM, 200 mM and 400 mM, removal by means of magnetic separation and examining the eluates photometrically for their DNA content.

Figure 5:
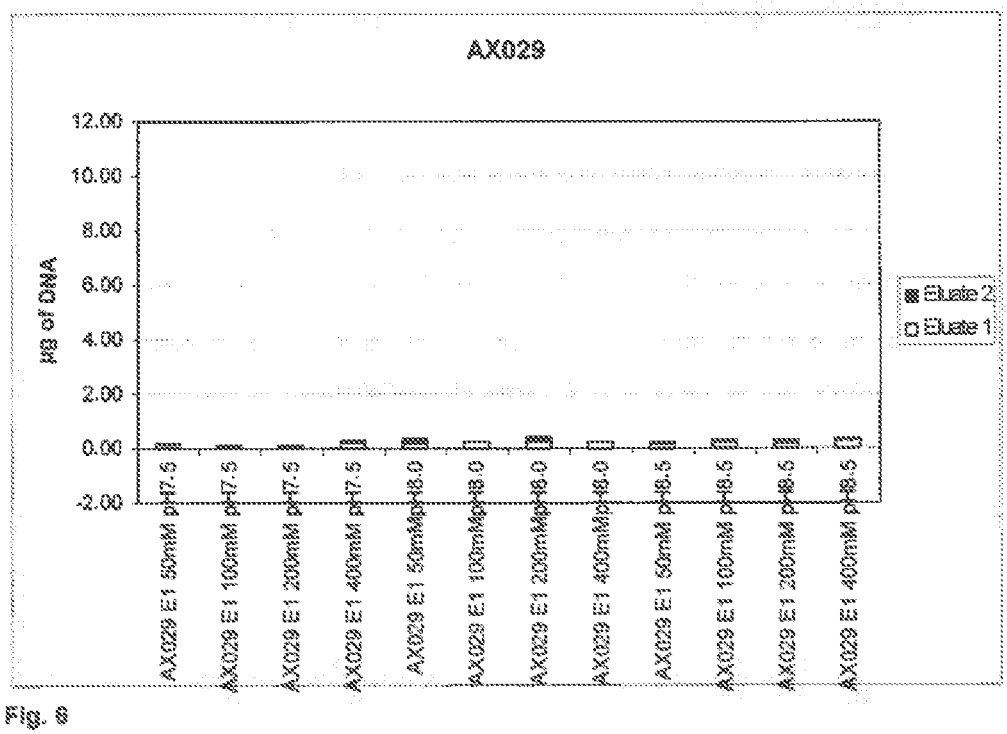

The results are depicted in FIG. 5.

G) Purification of Genomic DNA Using Spermine-functionalized Magnetic Polymers (AX 030)

For each purification, 2 mg of particles are suspended in 25 mM MES, 25 mM Tris, pH 6.2. This is followed by adding 10 µg of calf thymus genomic DNA (catalogue No. 89370, Fluka, Germany) in buffer "EB" and mixing by way of brief shaking. This is followed by magnetic separation and photometric examination of the. The residue is washed with 100 µl of Millipore water with magnetic separation to remove the supernatants, followed by eluting twice with in each case 50 µl of 50 mM TRIS buffer and 50 mM and 100 mM NaCl, respectively, pH 8.5. The DNA content of the individual eluates is then determined photometrically.

Figure 6:
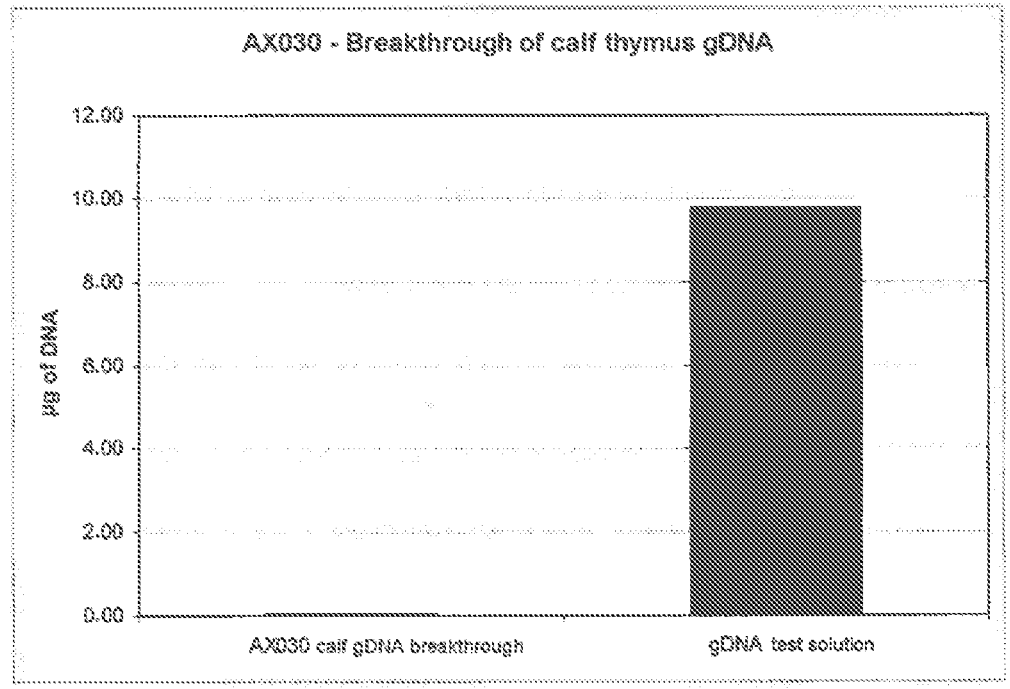
Figure 7:
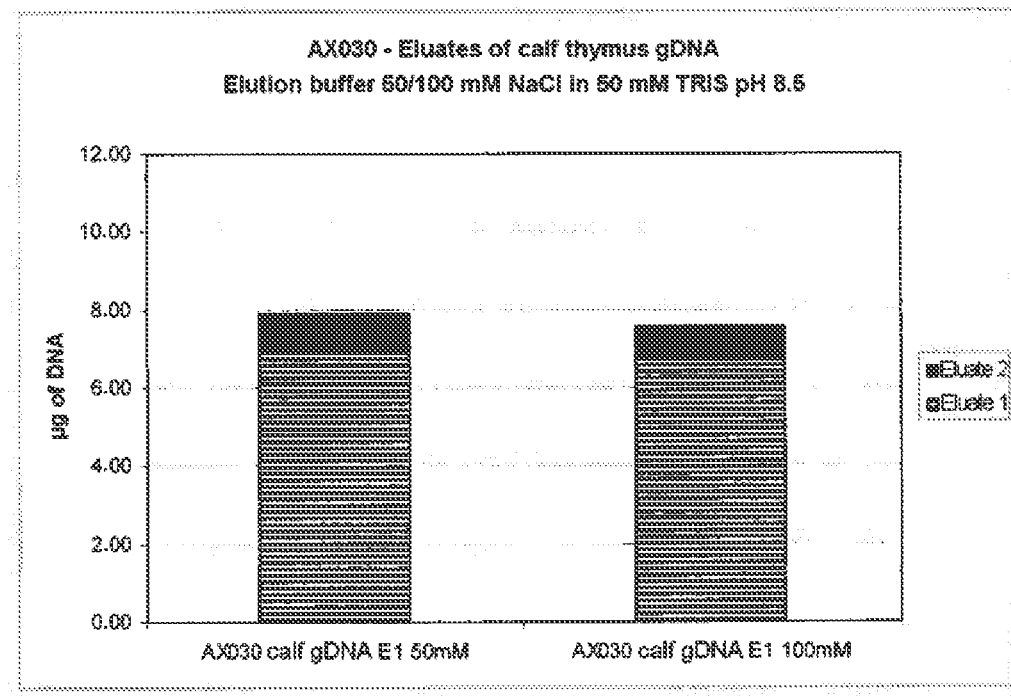

The results are depicted in FIG. 6 and FIG. 7.

H) Purification of RNA Using Spermine-functionalized Magnetic Polymers (AX 030)

For each purification, 2 mg of particles are suspended in 50 mM Tris buffer, pH 5.5. This is followed by adding 10 µg/prep. RNA (16S- & 23S ribosomal, Fermentas 41-1 g/l-ll) in 50 mM Tris buffer, pH 5.5. This is followed by mixing by way of brief shaking, magnetic separation and the supernatants are then examined photometrically for RNA. This is followed by washing twice with in each case 100 µl of RNase-free water and removing the supernatants by magnetic separation. This is followed by eluting twice with in each case 50 µl or 50 mM TRIS (RNase-free), pH 8.5 and 50 mM and 100 mM NaCl, respectively. The eluates are then photometrically examined separately.

Figure 8:
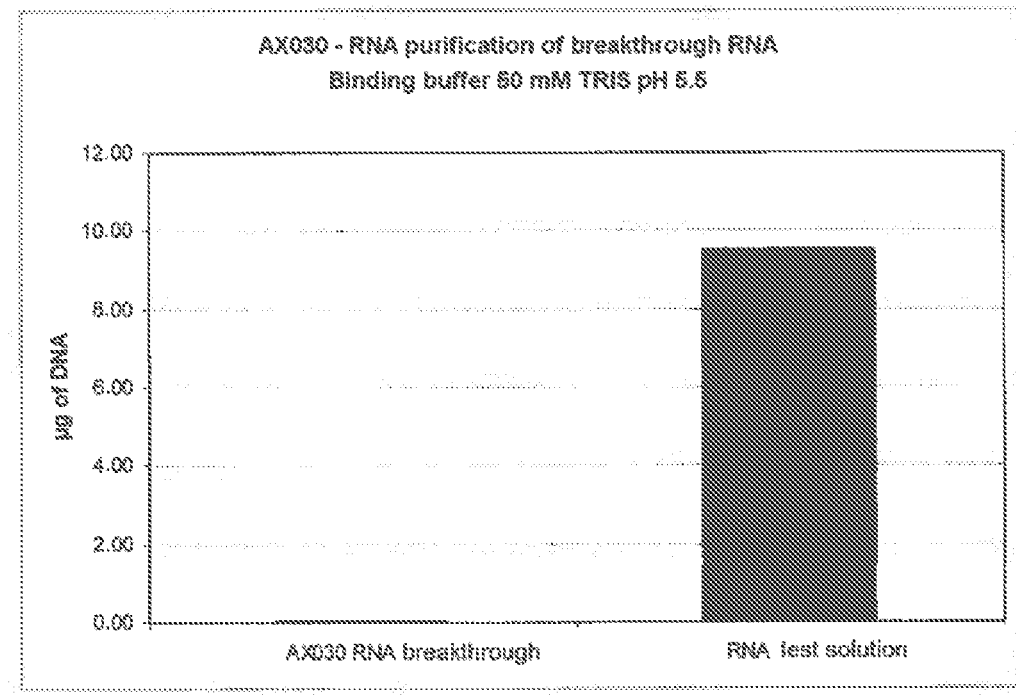
Figure 9:
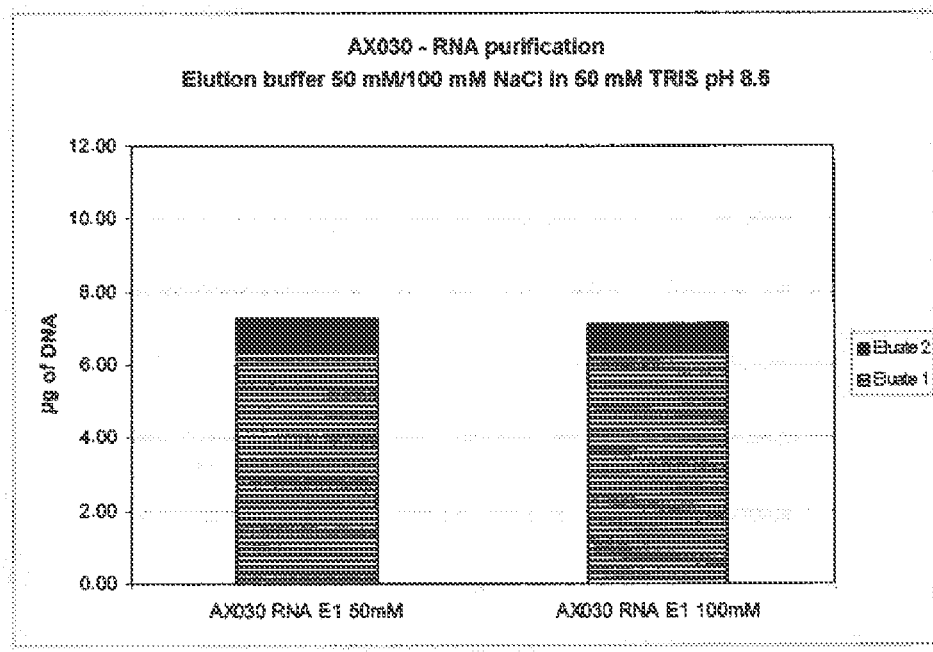

The results are depicted in FIG. 8 and FIG. 9.

I) Purification of Nucleic Acid Fragments Using Spermine-functionalized Magnetic Polymers (AX 030)

Preparation

The spermine-functionalized magnetic polymer particles are suspended in a binding buffer containing 25 mM MES, 25 mM Tris, pH 6.2, at a suspension density of 50 mg/ml. The beads are then washed another two times with this buffer, and the supernatants are removed by means of magnetic separation. Type pTZ19R plasmid DNA is required, of which 25 µg of DNA are to be used for 100 µl of buffer solution. First, all quantities for the reaction mixture are calculated, followed by introducing the missing amount of water to add up to 100 µl, adding the DNA, then the matching enzyme buffer for the enzyme solution (1 µl per 10 µl of total solution), then finally 3U of restriction enzyme (Hinf I, New England Biolabs, Cat. No. R0155S) per µg of DNA (usually 75 U correspond to 7.5 µl of enzyme solution). The mixture is left to incubate in a water bath or heat block at 37° C. for 90 minutes. This is followed by brief centrifugation using Quick-Run to 6000 U/min, and the samples are then frozen at −20° C. This restriction-digested DNA is a simple and rapid PCR replacement for assaying the PB buffers.

Procedure

For each sample, 8 µl of the PCR solution (corresponding to 2 µg of DNA) are admixed with 92 µl of 25 mM MES, 25 mM Tris, pH 6.2, and then with 25 µl of the magnetic silica gel suspensions, followed by vortexing for 10 seconds, admixing with 500 µl of 25 mM MES, 25 mM Tris, pH 6.2, and mixing. The mixture is incubated in a shaker for 2 minutes. This is followed by magnetic separation, discarding of the supernatant and washing twice with in each case 750 µl of Millipore water. This is followed by eluting first with 50 µl, then with 30 µl of 50 mM Tris/HCl, 50 mM NaCl, pH 8.5. The eluates are combined and examined photometrically, and also, by way of a gel, for DNA content.

Figure 10:
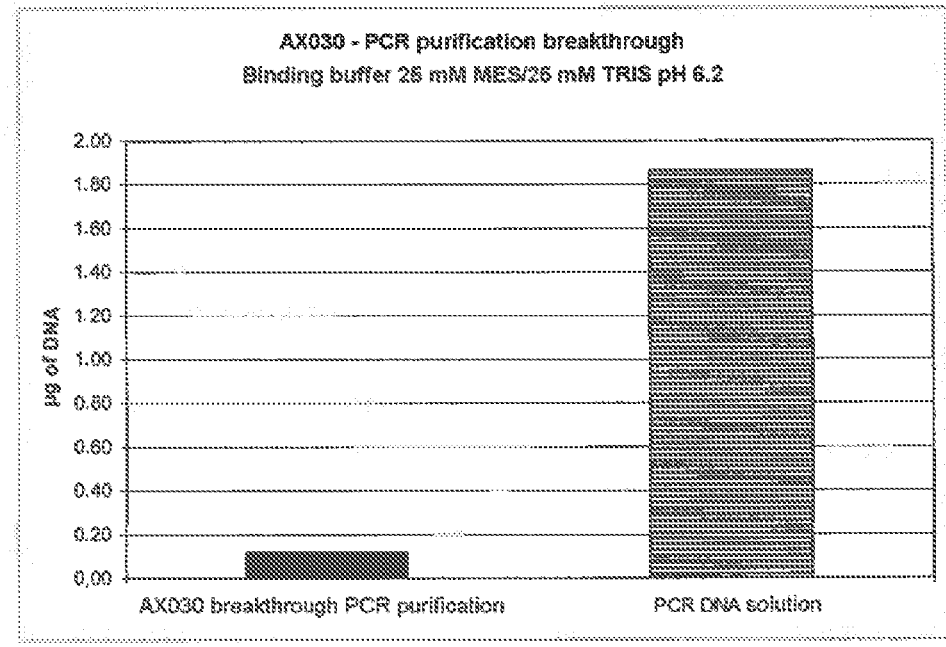
Figure 11:
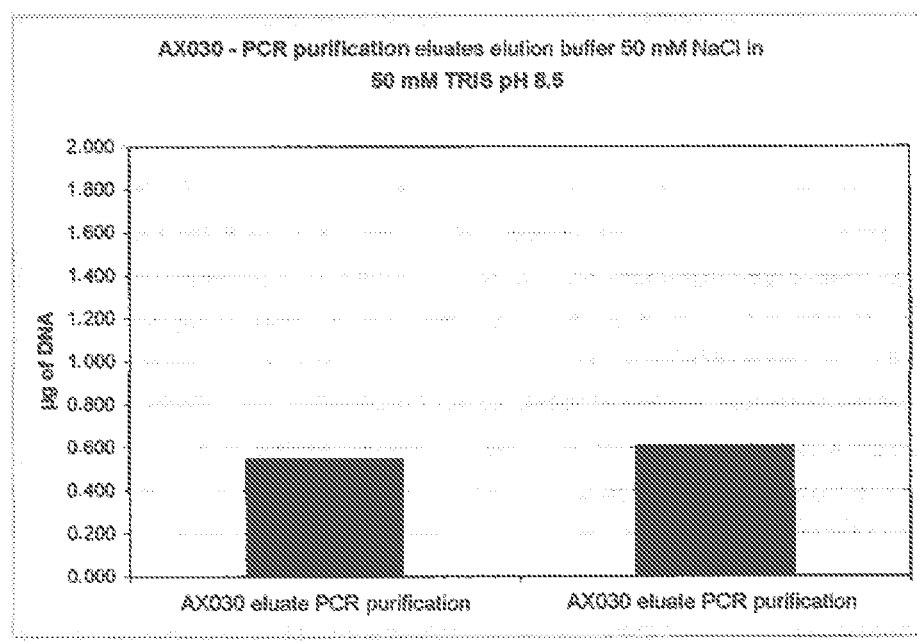
Figure 12:
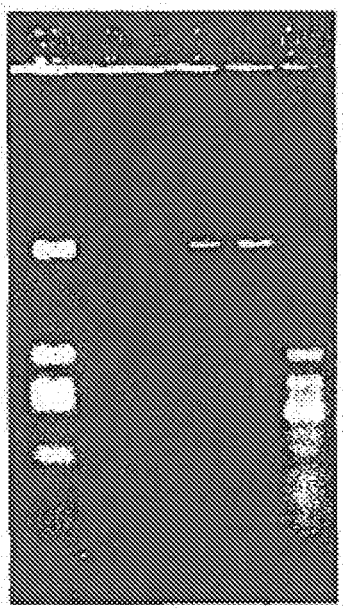

The results are depicted in FIG. 10, FIG. 11 and FIG. 12.

J) Purification of Genomic DNA from Blood Using Spermine-functionalized Magnetic Polymers (AX 040)

1 ml of lysis buffer (10 mM TRIS, polyethylene glycol p-(1,1,3,3-tetramethylbutyl)-phenyl ether sold under the trademark TRITON™ X-100, pH 9.0) and 10 µl of proteinase K are mixed. 1 mg of beads and 3.4 µl of water are suspended in 200 µl of bind buffer (1.5 M potassium acetate pH 4.0) at a suspension density of 26.6 mg/ml. 100 µl of thawed whole blood (citrate-stabilized) are admixed with the lysis buffer/proteinase mix in an Eppendorf cup and mixed well. This is followed by incubation at room temperature for 10 minutes. The beads are carefully resuspended in binding buffer. Of this, 240 µl are added to the lysed blood, followed by careful mixing by pipetting up and down. This is followed by incubation at room temperature for 1 min. The beads are magnetically separated. The supernatant is removed with care, For washing, 1 ml of washing buffer (water) is added, followed by careful mixing by pipetting up and down. After another magnetic separation, the supernatant is discarded. 1 ml of lysis buffer and 50 µl of binding buffer are added, mixed carefully and incubated at RT for 1 min. Magnetic separation is followed once more by washing with 1 ml of washing buffer and magnetic separation.

The purified DNA is eluted by adding 150 µl of elution buffer (10 mM TRIS*HCl pH 8.5) to the beads. The beads are resuspended by pipetting up and down several times. The beads are magnetically separated, the supernatant is removed, and the DNA is photometrically quantified.

Figure 13:
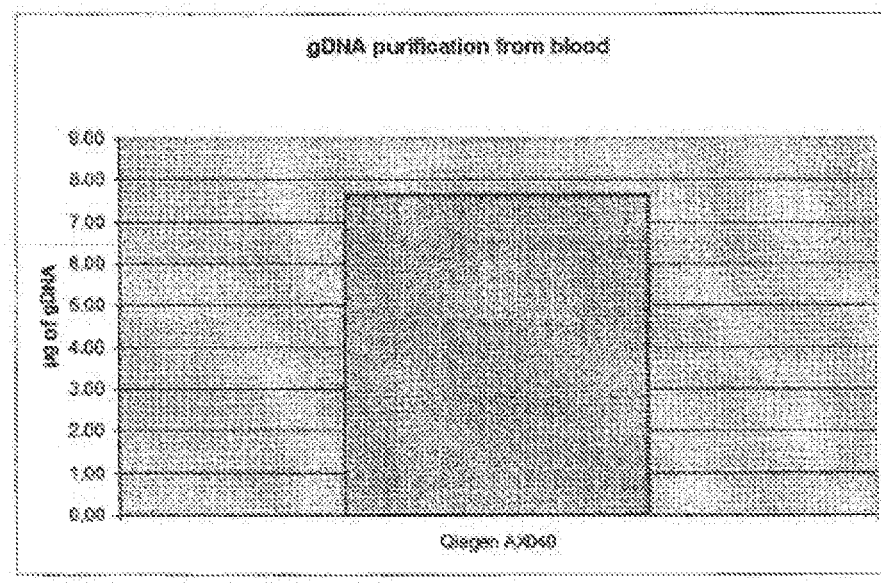

The results are depicted in FIG. 13.

5 µl of the eluate obtained above are subjected to RT-PCR. For this TAQMAN® β-actin control reagent (Applied Biosystems, No. 401846) and QUANTITECT® Probe PCR Mastermix (QIAGEN, No. 1019337) are used, with 12.5 µl of Mastermix, 2.5 µl of β-actin Probe (6-FAM), 2.5 µl of β-actin Forward Primer and 2.5 µl of β-actin Reverse Primer being applied.

Figure 14:
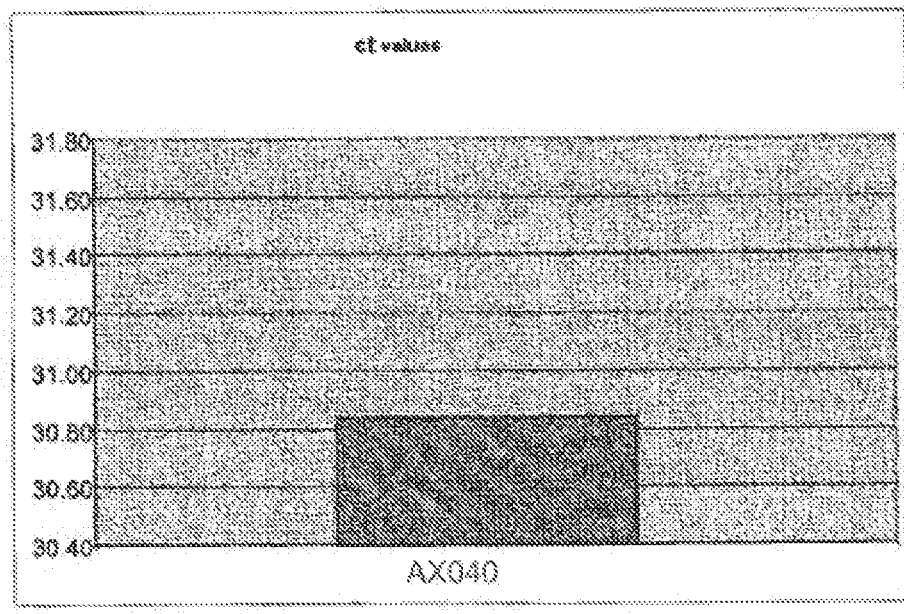

The results are depicted in FIG. 14.

The invention claimed is:

1. A method of purifying nucleic acids from a nucleic acid-containing sample, the method comprising:
   (a) contacting the nucleic acid-containing sample with a nucleic acid-binding phase comprising nucleic acid-binding groups covalently bound to a support, the nucleic acid-binding groups having one or more protonatable groups having a pKa from 9 to 12;
   (b) binding the nucleic acids to the nucleic acid-binding phase at a binding pH which is more than one pH unit below the pKa of at least one of the one or more protonatable groups; and
   (c) eluting the nucleic acids at an eluting pH which is above the binding pH, but one, or more than one, pH unit below the pKa of at least one of the one or more protonatable groups,
   wherein the nucleic acid-binding phase further comprises:
   (i) diluting groups, wherein the proportion of nucleic acid-binding groups relative to the diluting groups is <50%; and
   (ii) functional groups which are bound to the support and/or the nucleic acid-binding groups, and which functional groups have a negative charge during the eluting and promote the release of the nucleic acids at the eluting pH.

2. The method according to claim 1 wherein the functional groups are cation exchangers.

3. The method according to claim 1, wherein the binding comprises one or more of the following:
   (a) binding at a pH from 3 to 8, from 4 to 7.5, from 4.5 to 7, from 5.5 to 7, or from 6.5 to 7; and/or
   (b) binding at a salt concentration of less than 1 M.

4. The method according to claim 1, wherein the eluting comprises one or more of the following:
   (a) eluting at a pH of from 7.5 to 10, 8 to 9, or 8.2 to 8.8; and/or
   (b) eluting at a salt concentration of less than 1 M; and/or
   (c) eluting in a solution selected from the group consisting of water, biological buffers and organic buffers.

5. The method according to claim 1, further comprising washing the nucleic acid binding phase with a washing solution after the binding and before the elution of the nucleic acids.

6. The method according to claim 5 wherein the washing solution is water or an aqueous solution, the aqueous solution having a salt concentration of less than 400 mM.

7. The method according to claim 1, wherein the one or more protonatable groups comprise amino groups.

8. The method of claim 2, wherein the functional groups are acidic groups.

9. The method of claim 8, wherein the acidic groups are carboxyl groups.

10. The method of claim 7, wherein the one or more protonatable groups comprise from one to ten, two to eight, or two to six amino groups per protonatable group.

11. The method of claim 7, wherein the amino groups have a pKa of from 10 to 12.

12. The method of claim 7, wherein the amino groups are not conjugated to one or more electron density-reducing groups.

13. The method of claim 1, wherein the support is an organic polymer, hydrogel, or inorganic material.

14. The method of claim 13, wherein the support is an organic polymer selected from the group consisting of polystyrenes, polyacrylates, polymethacrylates, polyurethanes, nylon, polyethylene, polypropylene, polysaccharides, polybutylene and copolymers thereof.

15. The method of claim 13, wherein the support is a hydrogel selected from the group consisting of agarose, cellulose, dextran, cross-linked dextran gel, cross-linked allyl dextran N,N'-methylene bisacrylamide, and chitosan.

16. The method of claim 13, wherein the support is an inorganic material selected from the group consisting of silica gels, silica particles, glass, metal oxides, semi-metal oxides, boron oxide, magnetic particles and substrates with a metal surface.

17. The method of claim 16, wherein the inorganic material is a substrate with a gold surface.

18. The method of claim 1, wherein the nucleic acid-binding groups comprise primary and secondary amines.

19. The method of claim 18, wherein the nucleic acid-binding groups are spermine and/or spermidine.

20. The method of claim 1, wherein the one or more protonatable groups have, or are, ion exchangers.

21. The method according to claim 3, wherein the binding occurs at a salt concentration of 0.5 M or less, 0.25 M or less, or 0.1 M or less.

22. The method according to claim 4, wherein the eluting occurs at a salt concentration of 0.5 M or less, 0.25 M or less, 0.1 M or less, 50 mM or less, 0.25 mM or less, 0.15 mM or less, or 10 mM or less.

23. The method according to claim 5 wherein the washing solution is water or an aqueous solution, the aqueous solution having a salt concentration of 200 mM or less, 100 mM or less, 50 mM or less, or 25 mM or less.

24. The method according to claim 1, wherein the proportion of nucleic acid-binding groups relative to the diluting groups is ≤25%.

25. The method according to claim 1, wherein the proportion of nucleic acid-binding groups relative to the diluting groups is ≤15%.

* * * * *